(12) United States Patent
Foerster et al.

(10) Patent No.: US 6,660,008 B1
(45) Date of Patent: Dec. 9, 2003

(54) METHOD AND APPARATUS FOR ATTACHING CONNECTIVE TISSUES TO BONE USING A SUTURE ANCHORING DEVICE

(75) Inventors: Seth A. Foerster, San Clemente, CA (US); Minh Tran, Fountain Valley, CA (US); Norman S. Gordon, Irvine, CA (US)

(73) Assignee: Opus Medical, Inc., San Juan Capistrano, CA (US)

( * ) Notice: Subject to any disclaimer, the term of this patent is extended or adjusted under 35 U.S.C. 154(b) by 26 days.

(21) Appl. No.: 09/876,341

(22) Filed: Jun. 7, 2001

(51) Int. Cl.⁷ .................................................. A61B 17/56
(52) U.S. Cl. .......................................... 606/72; 411/34
(58) Field of Search ................... 606/72–74, 133–233; 411/34, 38, 43, 59

(56) References Cited

U.S. PATENT DOCUMENTS

| | | |
|---|---|---|
| 3,143,916 A | 8/1964 | Rice |
| 4,301,551 A | 11/1981 | Dore et al. |
| 4,467,478 A | 8/1984 | Jurgutis |
| 4,483,023 A | 11/1984 | Hoffman, Jr. et al. |
| 4,590,928 A | 5/1986 | Hunt et al. |
| 4,597,776 A | 7/1986 | Ullman et al. |
| 4,605,414 A | 8/1986 | Czajka |
| 4,672,957 A | 6/1987 | Hourahane |
| 4,712,542 A | 12/1987 | Daniel et al. |
| 4,772,286 A | 9/1988 | Goble et al. |
| 4,823,780 A | 4/1989 | Odensten et al. |
| 4,828,439 A | 5/1989 | Giannuzzi |
| 5,195,542 A | 3/1993 | Gazielly et al. |
| RE34,293 E | 6/1993 | Goble et al. |
| 5,275,176 A | 1/1994 | Chandler |
| 5,326,205 A | 7/1994 | Anspach, Jr. et al. |
| 5,330,468 A | 7/1994 | Burkhart |
| 5,441,508 A | 8/1995 | Gazielly et al. |
| 5,470,335 A | * 11/1995 | Du Toit ........................ 606/53 |
| 5,472,452 A | * 12/1995 | Trott ............................ 24/297 |
| 5,501,695 A | * 3/1996 | Anspach et al. .............. 411/34 |
| 5,531,792 A | * 7/1996 | Huene .......................... 411/24 |
| 5,571,104 A | * 11/1996 | Li ................................ 606/232 |
| 5,573,548 A | 11/1996 | Nazre et al. |
| 5,575,801 A | 11/1996 | Habermeyer et al. |
| 5,584,839 A | 12/1996 | Gieringer |
| 5,591,207 A | 1/1997 | Coleman |
| 5,645,589 A | * 7/1997 | Li ................................. 411/24 |
| D385,352 S | 10/1997 | Bales et al. |
| 5,681,333 A | 10/1997 | Burkhart et al. |
| 5,690,649 A | 11/1997 | Li |
| 5,697,950 A | 12/1997 | Fucci et al. |
| 5,702,397 A | 12/1997 | Goble et al. |
| 5,707,394 A | 1/1998 | Miller et al. |

(List continued on next page.)

FOREIGN PATENT DOCUMENTS

| | | |
|---|---|---|
| EP | 611557 | 8/1994 |
| FR | 2777442 | 10/1999 |
| FR | 2777447 | 10/1999 |
| WO | WO 9525469 | 9/1995 |

*Primary Examiner*—David O. Reip
*Assistant Examiner*—Victor Nguyen
(74) *Attorney, Agent, or Firm*—Stout, Uxa, Buyan & Mullins, LLP; Donald E. Stout

(57) ABSTRACT

A bone anchor and methods for using same to secure connective tissue, such as tendons, to bone are disclosed which permit a suture attachment that lies entirely beneath the cortical bone surface. The bone anchor of the invention incorporates a deformable body that creates an increased anchor body diameter after it is inserted into the cancellous bone and deployed beneath the cortical surface of the bone. The increased body diameter, by virtue of its intrinsic geometry, creates both axial and rotational fixation of the bone anchor or suture fixation point.

17 Claims, 11 Drawing Sheets

U.S. PATENT DOCUMENTS

| | | |
|---|---|---|
| 5,725,541 A | 3/1998 | Anspach, III et al. |
| 34,293 | 4/1998 | Goble et al. |
| 5,741,282 A | 4/1998 | Anspach, III et al. |
| 5,782,865 A | 7/1998 | Grotz |
| 5,797,963 A | 8/1998 | McDevitt |
| 5,810,854 A | 9/1998 | Beach |
| 5,843,111 A * | 12/1998 | Vijfvinkel .................... 604/22 |
| 5,860,978 A | 1/1999 | McDevitt |
| 5,868,789 A | 2/1999 | Huebner |
| 5,879,372 A | 3/1999 | Bartlett |
| 5,893,850 A * | 4/1999 | Cachia ........................ 606/63 |
| 6,007,567 A | 12/1999 | Bonutti |
| 6,013,083 A | 1/2000 | Bennett |
| 6,022,373 A * | 2/2000 | Li ............................... 606/232 |
| 6,045,572 A | 4/2000 | Johnson et al. |
| 6,156,056 A * | 12/2000 | Kearns et al. .............. 606/232 |

\* cited by examiner

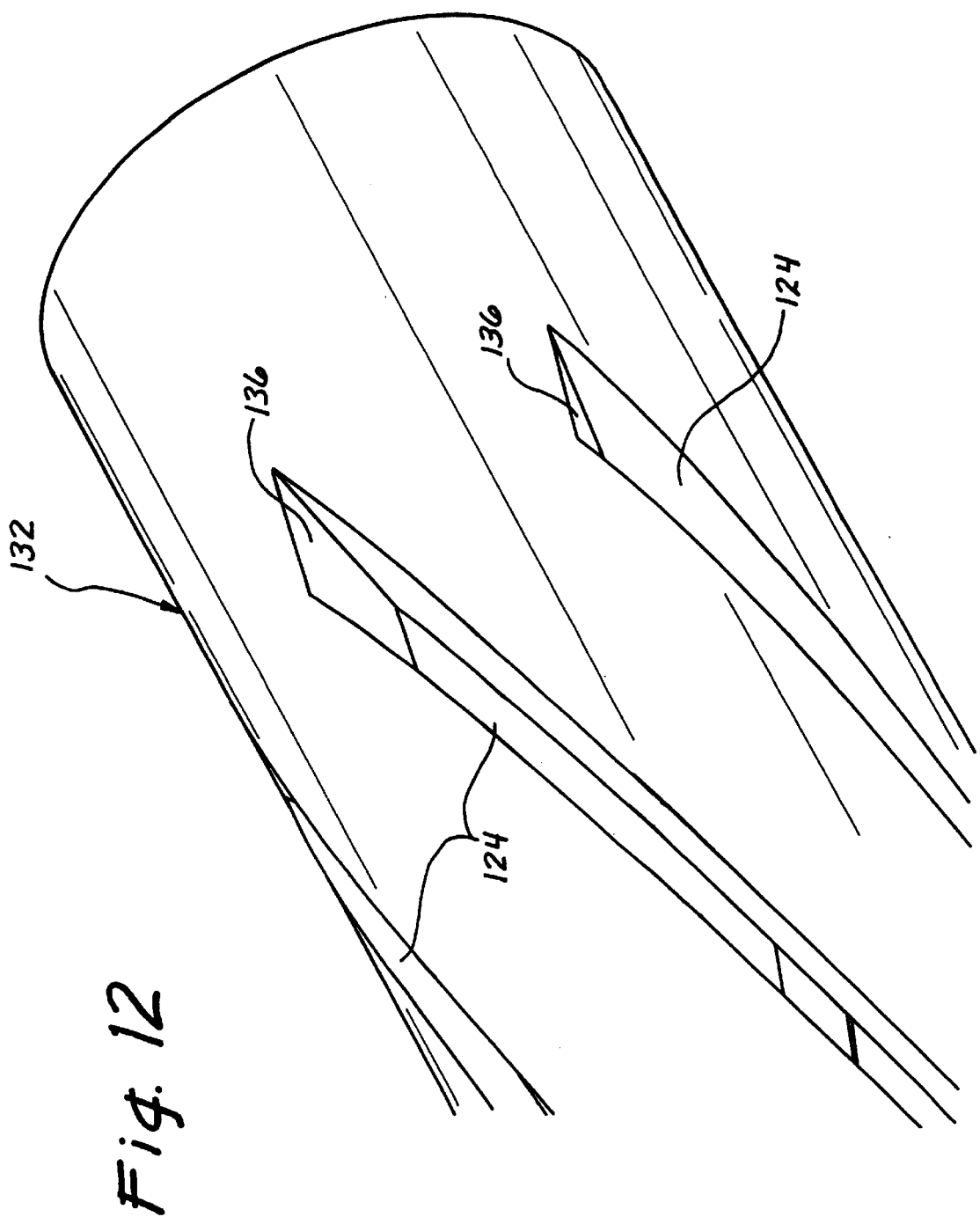

METHOD AND APPARATUS FOR ATTACHING CONNECTIVE TISSUES TO BONE USING A SUTURE ANCHORING DEVICE

This application is related to application Ser. No. 09/616,802, entitled *Method & Apparatus for Attaching Connective Tissues to Bone Using a Suture Anchoring Device*, filed on Jul. 14, 2000, and commonly assigned herewith.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort. The major stumbling block for many surgeons is the extreme difficulty in performing the procedure with the currently available tools and techniques.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. In one prior art approach that utilizes this physiological construct, the anchor is designed so that it has a longer axis and a shorter axis and is usually pre-threaded with suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out.

Examples of such an approach are seen in U.S. Pat. No. 5,879,372 to Bartlett and U.S. Pat. No. 6,007,4567 to Bonutti. Depending upon the density of the cancellous bone, these devices may be somewhat difficult to deploy. If the cancellous bone density is high, it is difficult to force the inserted anchor to rotated into a secured position.

It is possible to utilize other anchor geometry to take advantage of the cortical and cancellous bone interface. Various methods of creating an expanded or tortuous frontal area beneath the cortical surface have been described in the prior art. An example of this approach is seen is U.S. Pat.

No. 5,797,963 to McDevitt. This patent describes a subcortical anchor that utilizes a tapered flaring tool which deploys fingers circumferentially disposed about the periphery of the anchor to engage the cancellous bone and to resist retraction through the limited diameter hole in the cortical bone. A similar approach is disclosed in U.S. Pat. Nos. 5,690,649 and 6,022,373, both to Li. The Li patents describe an anchor that incorporates two cylindrical halves with fingers that are interdigitated. When a force is imposed on the two halves, the interlocked fingers cause the deflection and deployment of the concomitant adjacent fingers on the opposite half, creating the expanded areas that resists pull-out. In all of these designs, the expanding mechanism is adapted to resist axial loading, but there is no disclosure that they are capable of rotational fixation.

Still other prior art approaches have attempted to us a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

By now it should be clear that many existing fastener technologies have been adapted for use in creating an anchor point for sutures in bone. Screws, pop rivets, and the like are certainly adaptable to the wooden-like structure exhibited by bone. However, as previously discussed, bone also incorporates a structure that presents a hard, dense, outside surface and a softer, less dense core. Because of this structure, another type of fastener, commonly referred to as a "moly bolt" or "expandable bolt", may be adapted for use in the bone. These types of fasteners were originally designed for creating attachment points in plaster board walls where the wall is analogous to the hard cortical bone surface and the airspace or insulation space is analogous to the softer cancellous bone.

One example of such a fastener is shown in U.S. Pat. No. 4,828,439, to Giannuzzi. A screw anchor is disclosed which includes a four-legged compressible shank whose normal shape is diamond-like, the front legs of the shank being joined together by a front apex hinge and the rear legs being joined to the front legs by side apex hinges. The rear legs terminate in feet whose adjacent soles normally assume the form of an inverted V-inlet. A socket whose bore lies in axial registration with a hole in the front apex of the shank is secured by a pair of normally outstretched resilient webs to the respective rear legs. To install the anchor, its side apex hinges are manually compressed to collapse the shank into a tongue which is then inserted through a hole drilled in the wall until the socket is seated therein and the shank which is now behind the wall resumes its diamond-like shape. Then a screw for holding the fixture against the wall is inserted in the socket bore and turned therein until its tip is intercepted by the inlet which is dilated thereby to admit the screw. As the turning screw continues to advance, its crests engage the soles of the feet to force the rear legs apart and in doing so compels the shank to assume a triangular shape. At the conclusion of the screw advance, its tip is threadedly received in the hole of the front apex to create behind the wall a triangular truss in which the screw forms a central strut. It is clear in reference to this patent that the principal fixation is axial, and that no provision for rotational fixation is provided.

U.S. Pat. No. 5,893,850 to Cachia describes a fixation device of a type useful for connecting two or more bone segments during the healing process. In the preferred embodiment, the device comprises an elongate pin having a distal anchor thereon. This distal anchor is essentially an umbrella-shaped end to the pin that may be selectively collapsed for pushing through a hole drilled through the bone segments, and then deployed at the distal end of the hole to prevent the elongate pin from retracting back through the hole. A proximal anchor is co-axially and slidably disposed with respect to the pin, and fixable to accommodate different bone dimensions and permit appropriate tensioning of the fixation device. An additional embodiment may be used when the preferred embodiment is not possible to deploy. This situation may occur, for example, when there is not a distal bone surface to allow for the deployment of the umbrella-shaped pin end. This embodiment describes a construction with multiple, axially expanding strips that are configured to engage the cancellous bone to resist axial withdrawal of the main body of the anchor. The patent describes two or more sets of strips, as the disclosed function of the anchor is to fixate at least two bone segments together to promote healing of the bone. There is no mention of providing an anchor point to which a suture may be secured, nor is one contemplated.

Still another bone fixation device of interest is disclosed in U.S. Pat. No. 5,501,695 to Anspach, Jr. et al. In this patent, there is disclosed a bone anchor apparatus which comprises a rivet body having a lower annular portion 12 and an upper annular portion 100. The lower annular portion includes an outer surface formed as an extension of the outer surface of the upper annular portion. Because the thickness of the lower annular portion is less than that of the upper annular portion, the upper annular portion acts as an annular step or stop. A plurality of longitudinal slots are formed on the outer surface of the lower annular portion, and lengthwise ribs are formed between the slots. The apparatus comprises multiple components, including, additionally, a separate puller, including a head and a puller rod, which extends upwardly through the inner diameter of the lower and upper parts of the rivet's annular portions. In operation, the puller is actuated upwardly until it strikes the annular step, thereby axially compressing the lower annular portion so that the ribs are expanded radially outwardly.

There is shown in FIG. 8 of the '695 patent a disk 38 which includes apertures 40 for accommodating attachment of a suture 42 thereto. This disk, however, remains above the surface of the bone once the anchor is in place. While the '695 patent discloses an apparently functional device, it is complicated and difficult to use in the close quarters attendant to arthroscopic procedures.

It may be seen, then, that as different fasteners have been adapted for use in providing an anchor point for a surgical suture in conjunction with attaching soft tissues to bone, various problems and challenges have appeared. Although some of those problems and challenges have been addressed, not all of the requirements for simple, secure fixation have been met, particularly for creating a simple and facile apparatus and method for soft tissue fixation that may be deployed arthroscopically.

What is needed, therefore, is a new arthroscopic approach for providing an anchor point in bone structure, wherein the anchor resides completely below the superficial cortical bone surface, provides both axial and rotational fixation, is better for the patient, is uncomplicated to use, thereby saving time during the repair procedure, and is easily mastered by properly skilled personnel.

SUMMARY OF THE INVENTION

The present invention solves the problems outlined above by providing an innovative bone anchor and connective techniques which permit a suture attachment which lies entirely beneath the cortical bone surface. The anchor design permits easy and facile insertion into the bone, and simple and secure anchoring after deployment.

More particularly, there is provided by the inventive apparatus a means and method for attaching soft or connective tissue to bone, comprising a hollow cylinder having a longitudinal axis and a periphery which is adapted to be inserted into a hole pre-drilled into bone. The cylinder is adapted to have a plurality of slits and ribs running parallel to or roughly along the longitudinal axis of the cylinder and equally distributed about the diameter of the cylinder. For example, there may be 4 slits defining 4 ribs, equally spaced at 90° intervals around the cylinder. These ribs are predisposed to bend in a direction radially outwardly from their resting position when an axial load is placed upon the cylinder. The ribs bend in a characteristic fashion that has each end of the ribs bending outwardly, with the center of the rib bending at an angle approximately twice that of the ends, and in the opposite direction. Such structure creates a "flower" or an expansion of the outside diameter of the cylinder. The "flower" moniker is chosen because, as the ribs bend outwardly away from the body of the cylinder, they create "petals" around the periphery of the cylinder.

As previously mentioned, the structure of the bone in the humerus, for example, has a dense outer layer called the cortical bone, and a lacy, cellular inner structure called the cancellous bone. When the hole for the present invention is drilled in the bone, the hole extends through the cortical layer and into the cancellous layer. As it may be seen, if the anchor is placed such that the deployment of the ribs creating the flower is undertaken below the cortical layer and in the cancellous layer, it is not possible to remove the anchor proximally from the hole, as it is trapped underneath the cortical layer. This provides an extremely secure anchoring point that distributes any load placed upon it over a relatively large surface area when compared to anchors known in the prior art. This distribution of load is a significant advance in the art, and allows loads that typically would surpass the tensile strength of the sutures used to secure the tissues. In other words, because of the innovative design of the anchor, the sutures will break before the anchor is displaced.

In the present state of the art, as discussed supra, the sutures which are passed through the tissues to be attached to bone typically are threaded through a small eyelet incorporated into the head of the anchor and then secured by tying knots in the sutures. Although the anchor means herein described certainly are amenable to such attachment, if desired, an eyelet is by no means the only way that sutures may be secured to the bone anchor. Other means of attachment which allow for adjustable, releasable suture fixation that does not require knot tying is contemplated.

It may be seen that the geometry created by the present invention may provide both axial and rotational means of fixation for the bone anchor. The petals of the flower, as previously discussed, do prevent the anchor from being pulled axially out through the hole through which it was deployed. Also, because of the fact that the petals expand radially outward from the body of the anchor, they create anchor points within the cancellous bone that also resist rotational forces.

Additionally, the inventors have refined the "flower" concept to incorporate a unique and advantageous modification to the pattern of slits and ribs. By creating, in one preferred embodiment, the slits and ribs on a bias (in other words, at an acute angle when viewed relative to the axis of the body of the anchor), a different deployment mechanism is effected. With substantially axial ribs and slits, the ribs fold up in their characteristic fashion as previously described, i.e. each end of the ribs bending outwardly, with the center of the rib bending at an angle twice that of the ends and in the opposite direction and ultimately the two ends of the ribs flattening against each other. Instead, when the ribs are formed on the aforementioned bias, they tend to bend in a semi circular fashion and stack on top of each other, forming overlapping petals that create a substantial bulge in the body of the anchor.

More particularly, there is provided an apparatus for attaching connective tissue to bone, which comprises a body having a longitudinal axis, a proximal end, and a distal end, which is adapted to be inserted into a bone. The anchor body includes a plurality of spaced slits, preferably at least six, disposed about the periphery thereof, wherein each of the slits has a length, and a distance x between two adjacent slits at a first location along the length of each of the slits is smaller than a distance y between the two adjacent slits at a second location along the length of each of the slits. Preferably, the slits each comprise an end, wherein the first location is proximate to an end of each of the adjacent slits and the second location being in a middle region of each of the adjacent slits.

More preferably, each of the slits further comprises an angled surface at at least one, and preferably both ends thereof, wherein each of the angled surfaces, or "notches", extends depthwise into a wall forming the body. In preferred embodiments, the anchor body is a generally cylindrical body having an outer circumferential wall defining an inner lumen.

In some embodiments of the invention, the plurality of spaced slits are generally parallel to the longitudinal axis. In other, presently preferred embodiments, the plurality of spaced slits each lie at an acute angle relative to the longitudinal axis. The acute angle is preferably between 0 and 45 degrees.

The anchoring apparatus should include a plurality of spaced slits that are sufficient in number such that when an axial length of the body is shortened, a plurality of ribs which are disposed between each of the plurality of slits are caused to each expand radially to form respective petals, each of the petals overlap adjacent ones thereof.

In another aspect of the invention, there is provided an apparatus for attaching connective tissue to bone, comprising a body having a longitudinal axis, a proximal end, and a distal end, which is adapted to be inserted into a bone. The anchoring body includes a plurality of spaced slits disposed about the periphery thereof, each of the slits having a length and an angled surface at an end thereof, extending depthwise into a wall forming the body. Preferably, each of the slits has an angled surface at each end thereof, extending depthwise into the body wall.

In preferred embodiments, a distance x between two adjacent slits at a first location along the length of each one of the adjacent slits is smaller than a distance y between the same two adjacent slits at a second location along the length of each one of the adjacent slits. Such a configuration has been found to substantially reduce the axial forces required to deploy the anchor, once inserted into desired bone structure. Preferably, the first location is proximate to an end of each of the slits and the second location is in a middle region of each of the adjacent slits.

In yet another aspect of the invention, there is disclosed a method of fabricating an apparatus for attaching connective tissue to bone, which comprises a step of making a pattern of a bone anchor using a bio-compatible material. A plurality of spaced slits are disposed across a width of the pattern, such that adjacent ones of the slits are closer together at a first location along a length thereof and being farther apart at a second location along the length. The pattern is then formed into an anchor body, which is preferably generally cylindrical. The first location is preferably near an end of each of the respective adjacent slits and the second location is in a middle region of each of the respective adjacent slits.

Preferably, the method includes an additional step of forming an angled surface extending depthwise into the pattern at an end of each of the spaced slits, and, more preferably, at each end of each of the spaced slits. In order to form the slits in the aforementioned manner, it is preferred that a cutting wheel be used to form the spaced slits.

In still another aspect of the invention, there is disclosed a method of fabricating an apparatus for attaching connective tissue to bone, which comprises steps of making a pattern of a bone anchor using a bio-compatible material, and forming a plurality of spaced slits across a width of the pattern, such that an end of each of the slits includes an angled surface extending depthwise into the pattern. The pattern is then fabricated into an anchor body.

The invention, together with additional features and advantages thereof, may best be understood by reference to the following description taken in conjunction with the accompanying illustrative drawing.

BRIEF DESCRIPTION OF THE DRAWINGS

FIG. 12 is an enlarged detail view of a portion of the bone anchor shown in FIG. 11.

DESCRIPTION OF THE PREFERRED EMBODIMENT

Figure 1:
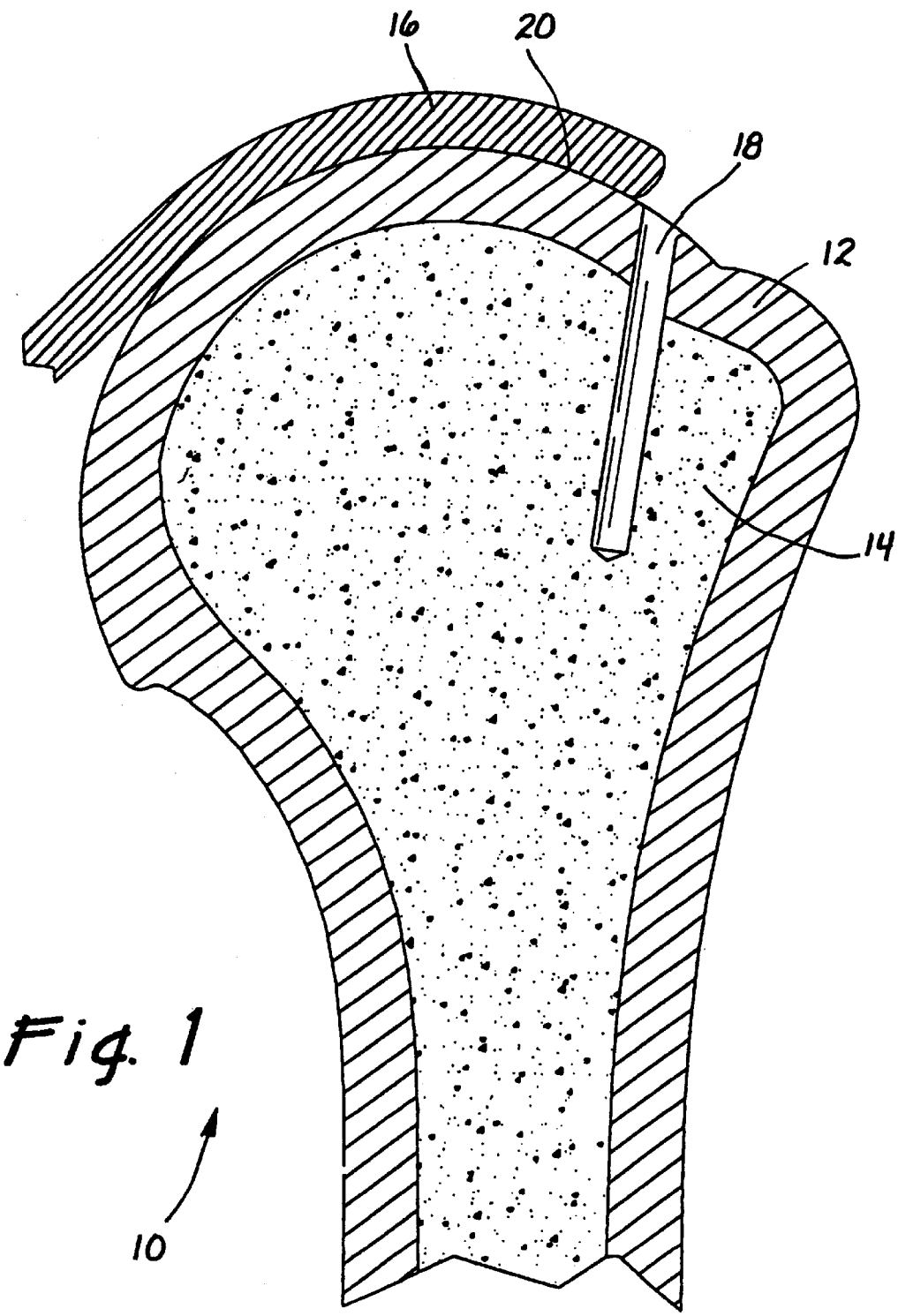
FIG. 1 illustrates a humerus and a tendon to be attached thereto in cross-section.

Referring now more particularly to the drawings, there is shown in FIG. 1a partial cross-sectional view of a humeral head 10 which includes an outer surface of cortical bone 12 and inner cancellous bone 14. A rotator cuff tendon 16 is disposed across the surface of the cortical bone 12. A blind hole 18 has been made, preferably by drilling, through a desired location on the cortical bone 12 and into the cancellous bone 14. This illustration is intended to provide a simple overview of the physiological elements and structure involved in a typical situation wherein reattachment of connective tissue such as the tendon 16 to the cortical bone 12 is desired. It is to be understood that the proximity in the illustration of the rotator cuff tendon 16 to the cortical bone 12 is merely exemplary, and that the rotator cuff tendon 16 is not attached to the cortical bone 12 at the interface 20 between the two.

Figure 2A:
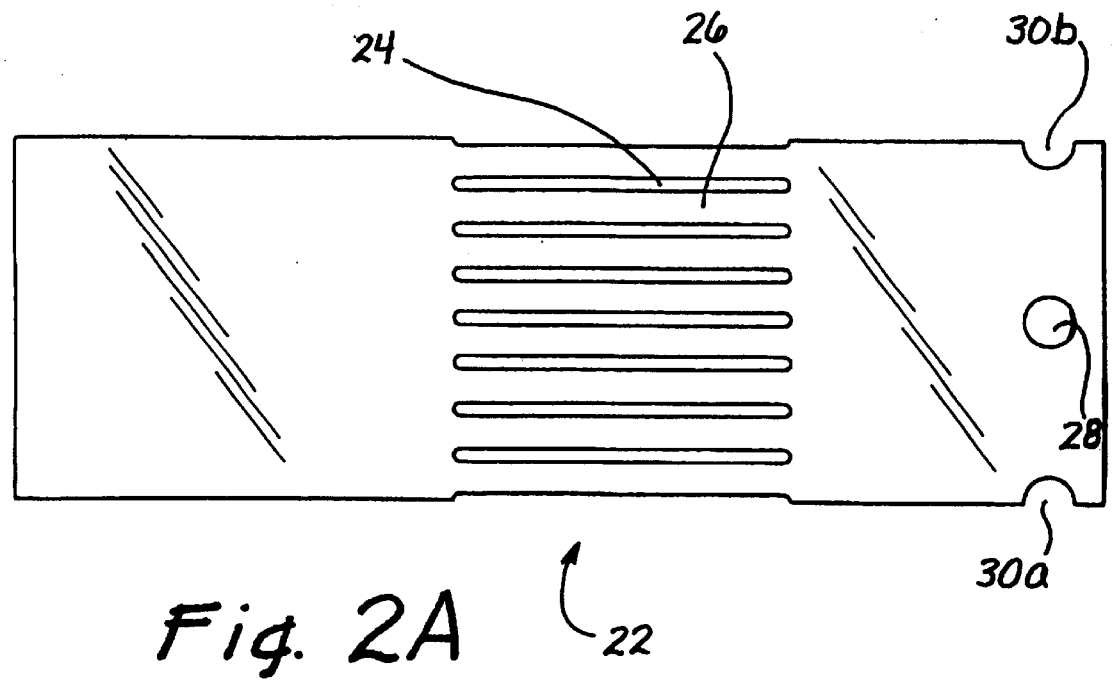
FIG. 2A is a plan view of a flat pattern to be formed into a bone anchor of the present invention.

Referring now to FIG. 2A, there is illustrated a flat pattern 22 of a bone anchor constructed in accordance with an embodiment of the present invention, including slits 24 and ribs 26 which are formed by the pattern of slits 24, together with a hole 28 and half holes 30a, 30b, aligned across the width of the pattern 22 at one end thereof. Such flat pattern 22 may be fabricated from any material suitable for implantation into the body as is known in the art, such as stainless steel 316L, and may be formed by flat stamping or photochemical machining or the like.

Figure 2B:
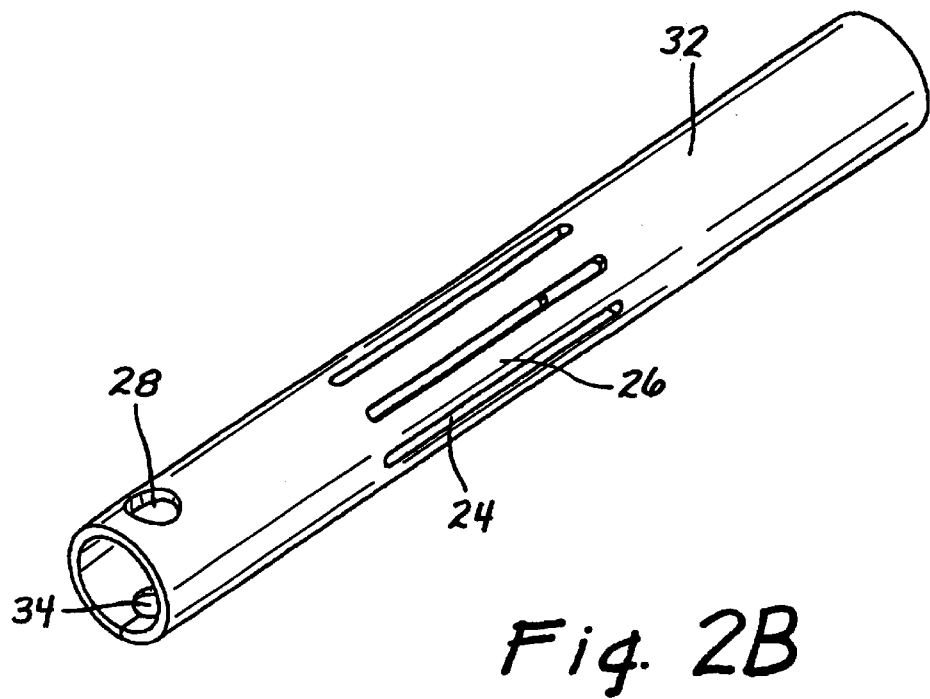
FIG. 2B is a perspective view of the flat pattern illustrated in FIG. 2A which has been roll formed into a cylinder.

Referring to FIG. 2B, the flat pattern 22 has been roll formed into a cylindrical body 32, which includes the slits 24 and ribs 26 seen in FIG. 2A, as well as the hole 28, and the half holes 30 which are now formed into a single hole 34, as a result of the roll forming process. It is to be understood, of course, that the flat form of the anchor has been shown for informational purposes as to one possible method of fabrication, and is not to be deemed limiting. Clearly, to those skilled in the art, many other methods of manufacture, such as laser cutting drawn hypodermic tubing, or deep draw progressive die stamping, may be employed. One particularly preferred method of manufacture, wherein a cutting wheel is employed to create the slits, is discussed below in connection with FIGS. 11 and 12.

Figure 3:
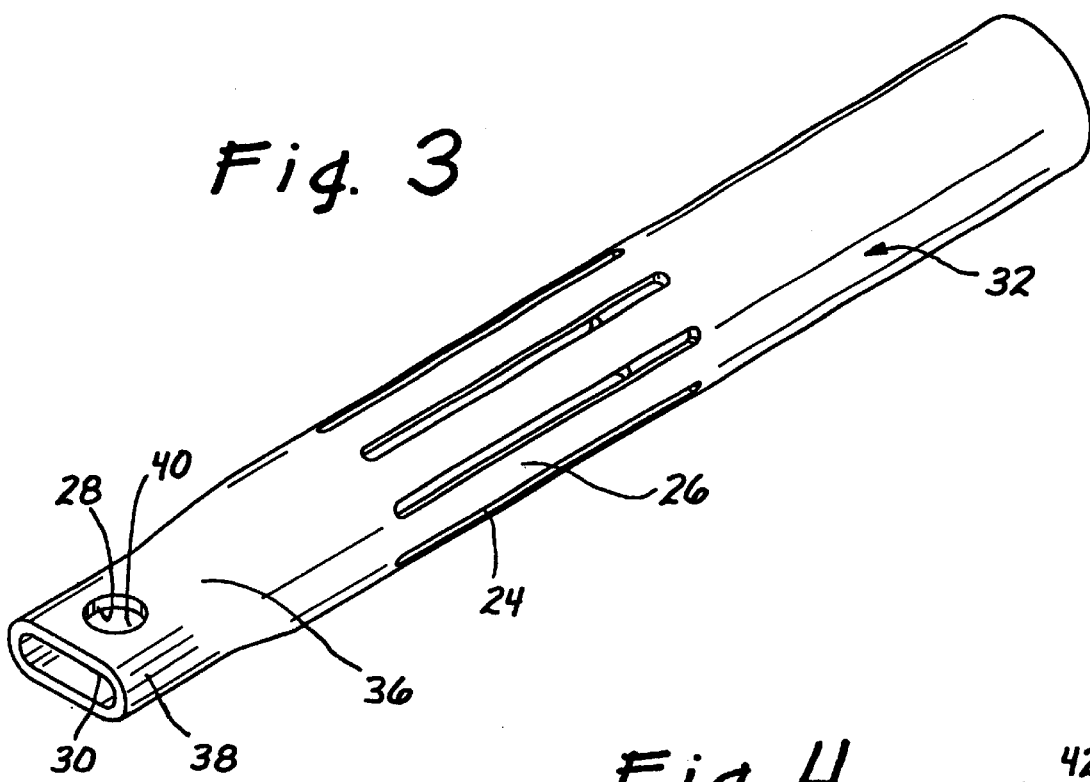
FIG. 3 is a perspective view of the structure illustrated in FIG. 2B, coined into a bone anchor of the present invention.

FIG. 3 shows the cylindrical body 32 of FIG. 2B, but it has now been coined to form a neck 36 at a proximal end 38, such that the hole 28 and the single hole 34 are aligned with each other to form a conduit 40 for suture to be passed through, to thereby provide an anchor point for the suture. How this anchor point is used will be more fully described below in connection with subsequent drawing figures.

Figure 4:
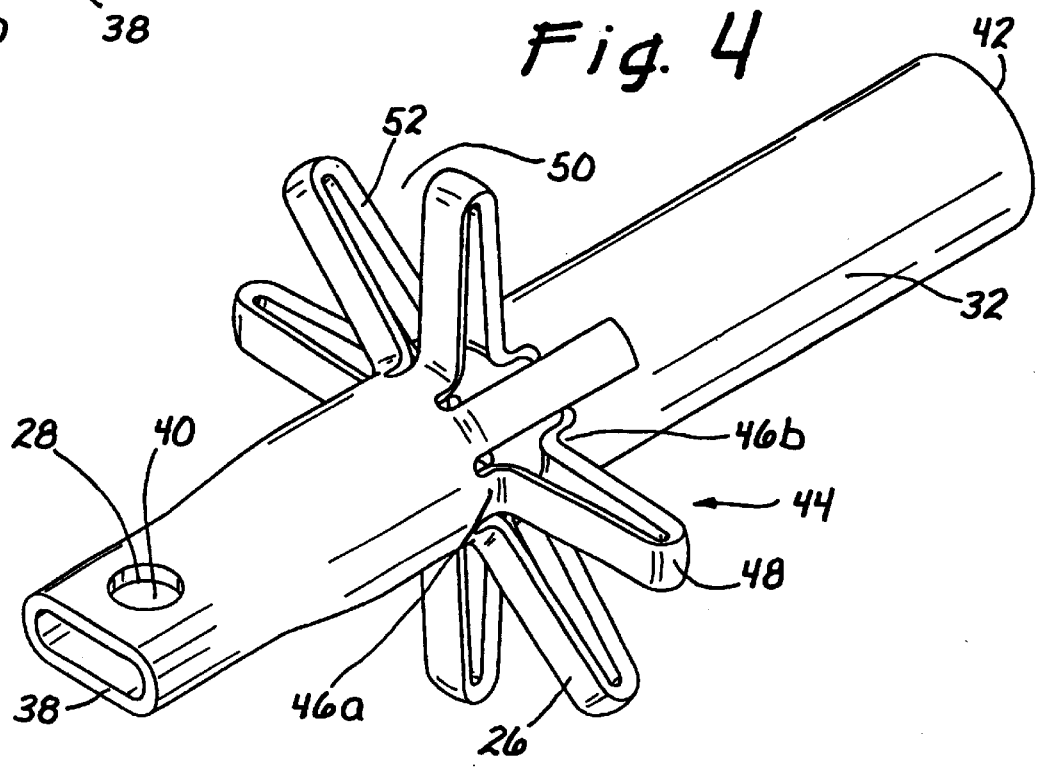
FIG. 4 is a perspective view of the bone anchor of FIG. 3 after deployment in accordance with a method of the present invention.

The bone anchor of FIG. 3 is shown in its undeployed state, with the cylindrical body 32 further having a distal end 42. Referring, however, to FIG. 4, it may be seen that the geometry of the ribs 26 has now been changed such that the ribs 26 have been bent to form one petal 44 that includes roots 46a, b and an apex 48. It is to be understood that although this description of the petal 44 is singular, it is clear that the geometry and configuration of the anchor includes multiple petals, and that this description therefore is applicable to all of the petals. In fact, in preferred embodiments a minimum of five petals, comprising, of course, six ribs and six associated slits, are employed, for reasons to be discussed hereinbelow.

The deformation of the ribs 26 is accomplished by imposing a compressive force on the distal end 42 and the proximal end 38 of the cylindrical body 32. Because each of the ribs 26 act as an independent column, when the compressive force is imposed, they eventually bend as a result of column buckling. After the onset of such buckling, the characteristic geometry has an angle of buckling at the apex 48 of the petal 44 which is equal to the sum of the angles at the roots 46a, b. At the formation of the petals 44, interstices 50 are created between the petals 44. The interstices 50 are important to the creation of a rotational fixation moment, in that edges 52 of the petals 44 are in direct contact with the cancellous bone as the flower is formed. The apex 48 creates a channel in the cancellous bone that traps material in the interstices 50 of the flower. Any rotational moment imposed on the bone anchor is resisted by the petals 44, and specifically by the edges 52 of the petals 44.

Figure 5:
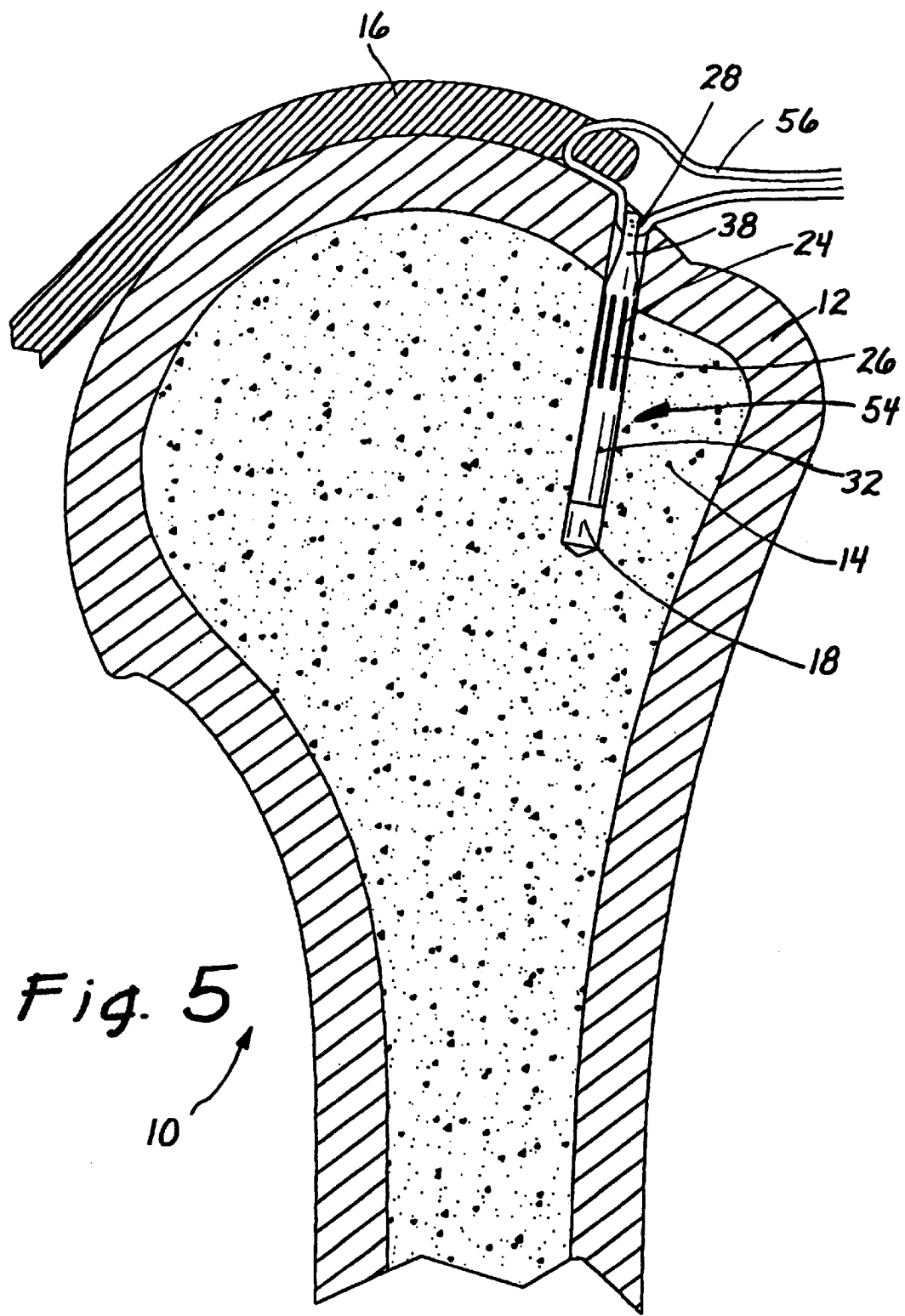
FIG. 5 is a cross-sectional view showing the bone anchor of FIG. 3 inserted into a hole drilled into the humerus of FIG. 1, according to a method of the present invention.
Figure 6:
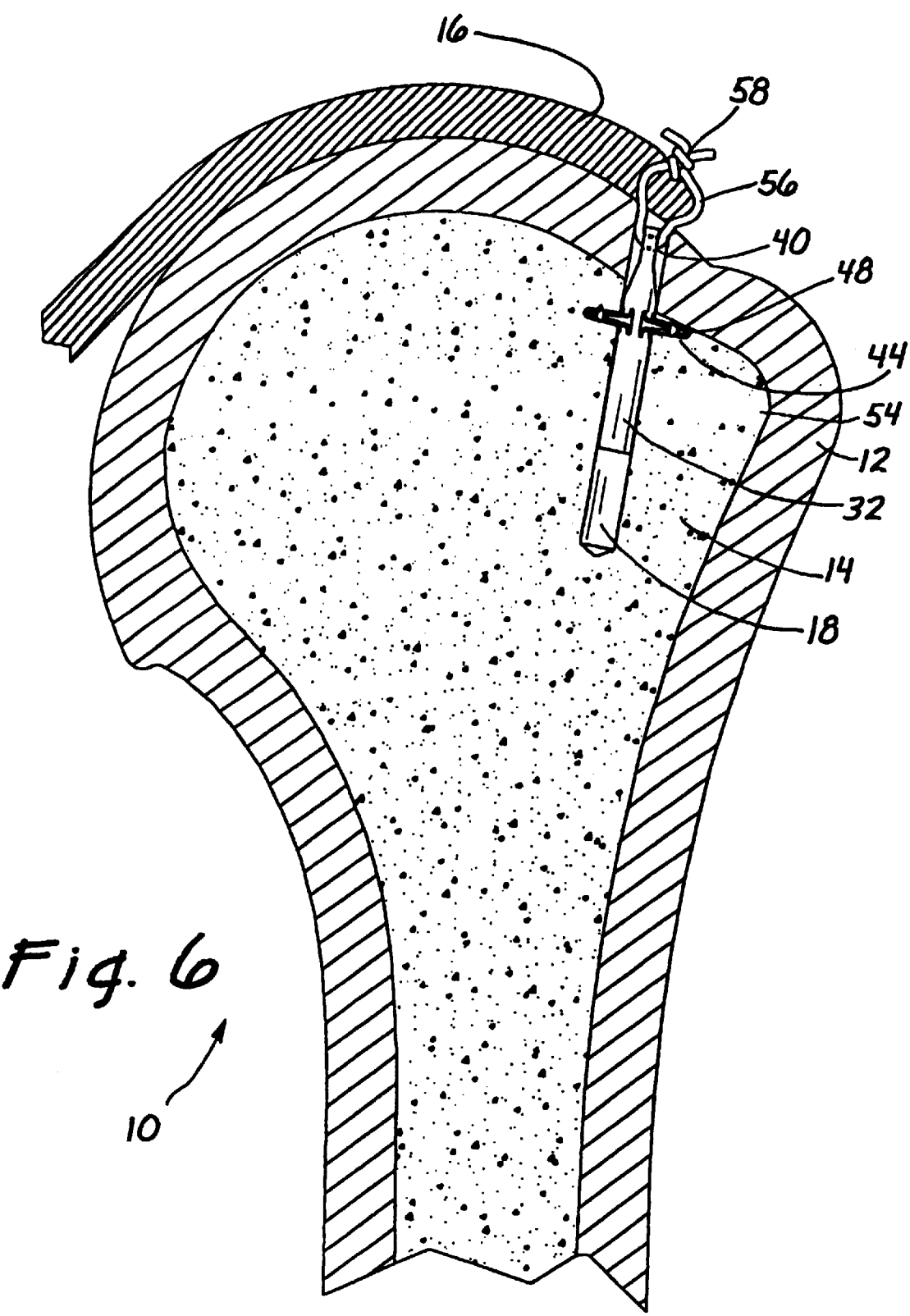
FIG. 6 is a cross-sectional view of the bone anchor of FIG. 5 after it has been deployed.

Referring to FIGS. 5 and 6, it can be seen how the inventive apparatus can be used as a bone anchor for attachment of soft tissues to bone. FIG. 5 illustrates a bone anchor 54 of the type shown in FIGS. 2–4 that has been inserted into the drilled hole 18 in the humeral head 10. The bone anchor 54 includes slits 24 and ribs 26 on a cylindrical body 32, as previously described. A length of suture 56 has been passed through the conduit 40 at the proximal end 38 of the bone anchor 54, and also stitched through the soft tissue represented by the rotator cuff tendon. The stitching process may be accomplished by any known means, and any known suture stitch may be employed, the objective being to ensure a secure stitch so that the suture is not inadvertently separated from the tendon after completion of the repair procedure, necessitating re-entry to the surgical site. In preferred approaches, the suture is attached to the soft tissue using a "mattress stitch", which is well known in the art as being a particularly secure stitch which is unlikely to fail postoperatively. Preferably, a suturing instrument is inserted into the trocar to perform the aforementioned suturing step. A preferred suturing approach is taught in co-pending application Ser. No. 09/668,055, entitled *Linear Suturing Apparatus And Methods*, filed on Sep. 21, 2000, expressly incorporated herein by reference and commonly assigned herewith.

After insertion into the drilled hole 18, the slits 24 and ribs 26 are in position in the cancellous bone 14 and below the surface of the cortical bone 12.

Now referring particularly to FIG. 6, the bone anchor 54 is illustrated in its deployed state. The slits 24 and ribs 26 have been converted into petals 44, and the apex 48 of each petal 44 has dug its way into the cancellous bone 14. The petals create a large surface area that bears against the underside of the cortical bone 12, and prevents the bone anchor 24 from being retracted proximally out of the drilled hole 18 in the cortical bone 12. The suture 56 has been tied into a knot 58, or otherwise tensioned, to thereby approximate the rotator cuff tendon 16 against the cortical bone 12. In this respect, while the inventive bone anchoring system has been illustrated in conjunction with various suture anchoring systems, it may also be desirable in some applications to use the inventive system in connection with an entirely different suture anchoring approach, such as the approach illustrated, for example, in co-pending U.S. patent application Ser. No. 09/781,793, entitled *Method & Apparatus for Attaching Connective Tissues to Bone Using a Knotless Suture Anchoring Device*, filed on Feb. 12, 2001, commonly assigned herewith and expressly incorporated by reference herein.

Figure 6A:
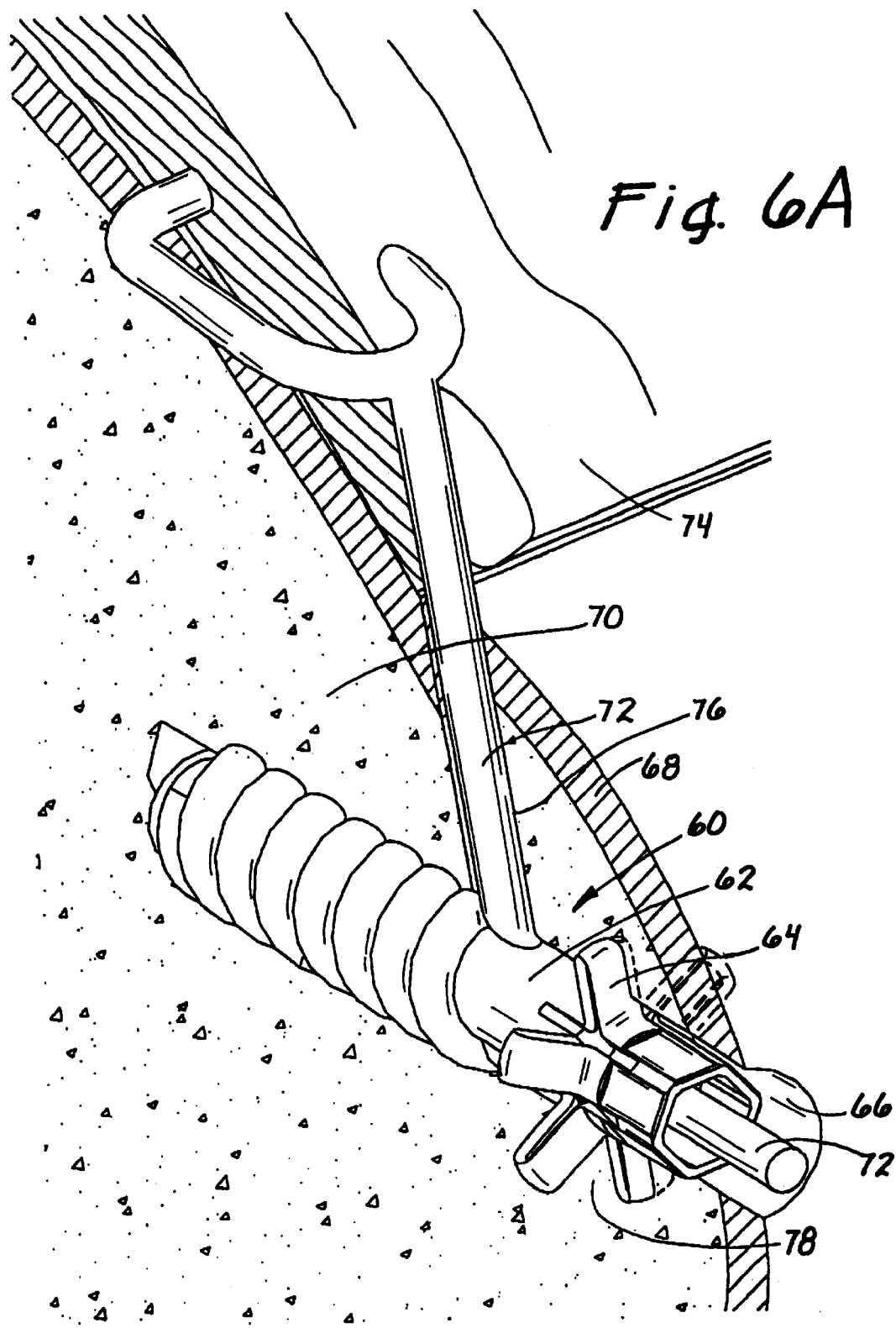
FIG. 6A is a perspective view of an alternative application for the bone anchor of the present invention.

As previously described, the inventive anchor fixation structure may be used not only to provide axial fixation, but also rotational fixation. Referring now to FIG. 6A, it can be seen how the petals 44 may create a rotational fixation structure. As previously noted, the contents of commonly assigned U.S. patent application Ser. No. 09/475,495 have been incorporated in their entirety in the present application. In that application, there is disclosed a unique bone anchoring system which utilizes an anchor structure that mimics a winch in order to create the fixation point and create tension in the sutures that are disposed through the tendon or soft tissue to be attached to bone. This novel system has the additional structural requirement of rotational fixation, as the suture is wrapped around the anchor body to create the aforementioned fixation and tension.

Accordingly, in FIG. 6A there is shown a bone anchor 60 which includes an anchor body 62 and petals 64. The bone anchor is inserted into a drilled hole 66 in the bone through cortical bone 68 and into cancellous bone 70. A suture 72 is passed through a tendon 74, threaded through a slit 76 in the bone, and is wrapped around the anchor body 62 by rotation of the anchor body 62. As previously discussed, the formation of the petals 64 create interstices 78 in the cancellous bone 70, which in turn provides a rotational moment about the axis of the anchor body 62. The created rotational moment resists any rotational force imposed by the suture 72 on the anchor body 62. it is important to note that this anti-rotational structure is deliberately created by judicious selection of petal geometry, i.e. the number of petals, how far they extend from the body 62, the breadth of their shoulders, and the thickness of the material from which they are fabricated. These factors affect the size and shape of the interstices that are formed between the petals, and, of course, the concomitant rotational moment that may be developed thereby.

More particularly, the inventors have found that a minimum of six ribs, forming six petals, are preferably employed, in order to ensure that the interstices between expanded ribs are not too large to be effective in containing trapped cancellous bone material, which functions in resisting applied rotational forces. A greater number of petals are also preferred to provide adequate expanded surface area to resist any applied rotational forces, as well as to provide a sufficiently strong expanded structure to adequately resist applied pullout forces. On the other hand, too many ribs, and consequent petals, will result in interstices which are too small to effectively trap an adequate amount of cancellous bone material.

Figure 7:
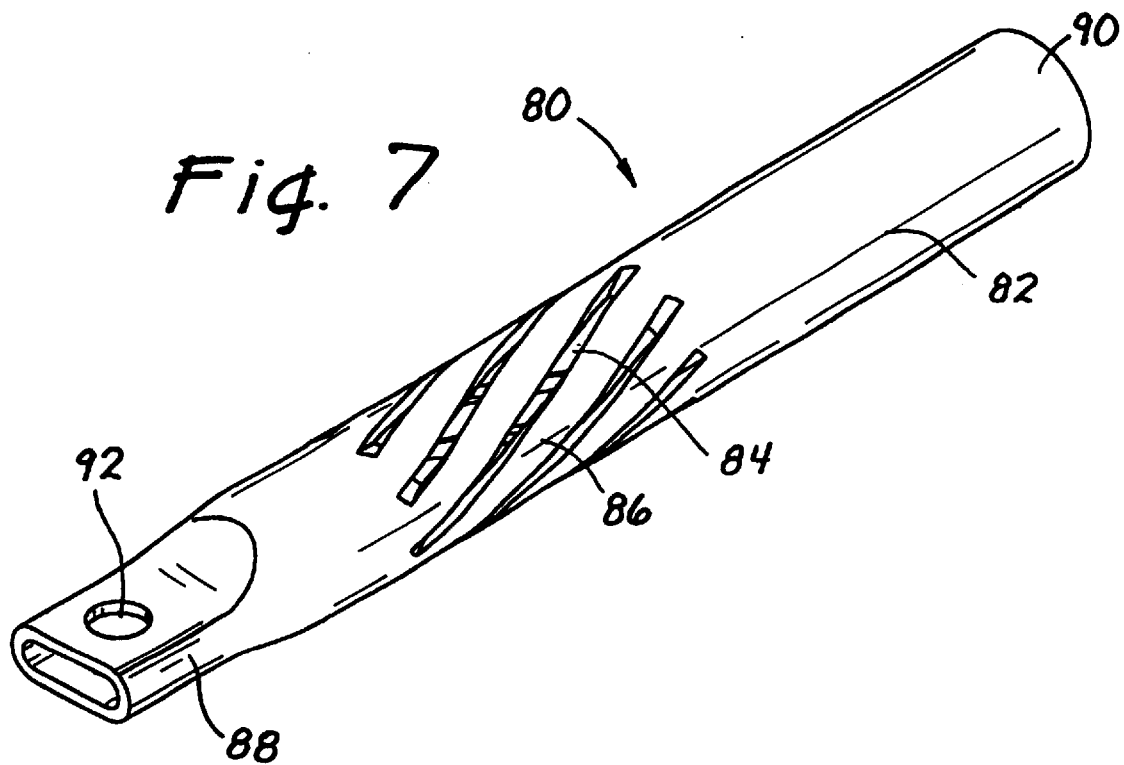
FIG. 7 is a perspective view of an alternative embodiment of the bone anchor of the present invention.

Another embodiment of the present invention may be seen by referring to FIG. 7, where there is illustrated a bone anchor 80 which includes a cylindrical body 82, into which slits 84 have been formed, creating ribs 86. The bone anchor 80 also includes a proximal end 88, a distal end 90, and a suture conduit 92. As may be observed from FIG. 7, the slits 84 have been formed at an acute angle (i.e. between 0 and 90 degrees, and preferably less than 45 degrees) to the axis of the cylindrical body 82. As before, it is to be understood that in referring to a single slit 84 or rib 86, we are also referring to the multiplicity of slits 84 and ribs 86 that are formed in the cylindrical body 82, as a single slit 84 or rib 86 is representative of each of the slits 84 or ribs 86. In other words, each petal has the same geometry and physical behavior, though the precise number of slits and ribs may vary in different embodiments, without deviating from the overall inventive concept. It may also be observed that the materials and construction of this embodiment of the bone anchor may be chosen using criteria similar to those described earlier with respect to alternate embodiments.

Figure 8:
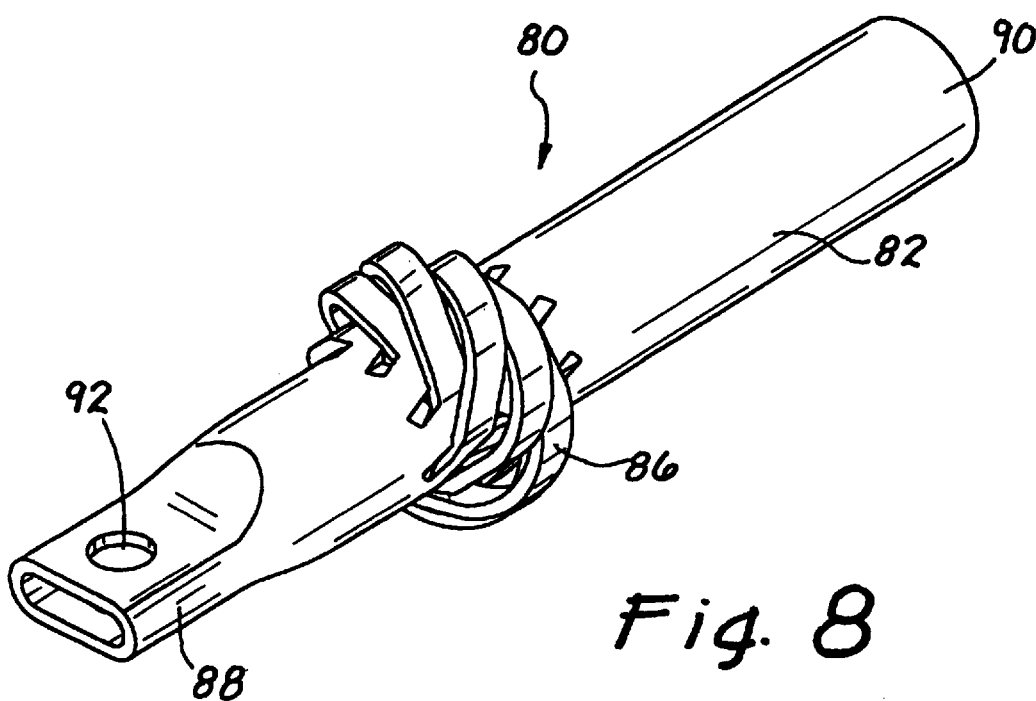
FIG. 8 is a perspective view of the bone anchor of FIG. 7 in a deployed state.

As may be seen by referring now to FIG. 8, as a compressive force is impressed on the distal end 90 and the proximal end 88, the ribs 86 buckle and deform into the characteristic shape shown. Because of the bias cut on the slits 84, instead of buckling in a linear fashion like the ribs 26 of FIG. 6, the ribs 86 buckle such that they take on a semi-circular shape, and adjacent ribs overlap and support each other. The inventors have found that a minimum of six ribs should be employed to obtain this important overlapping feature, which feature is significant in the configuration of an anchor point for a suture, as will be described hereinbelow.

Figure 9:
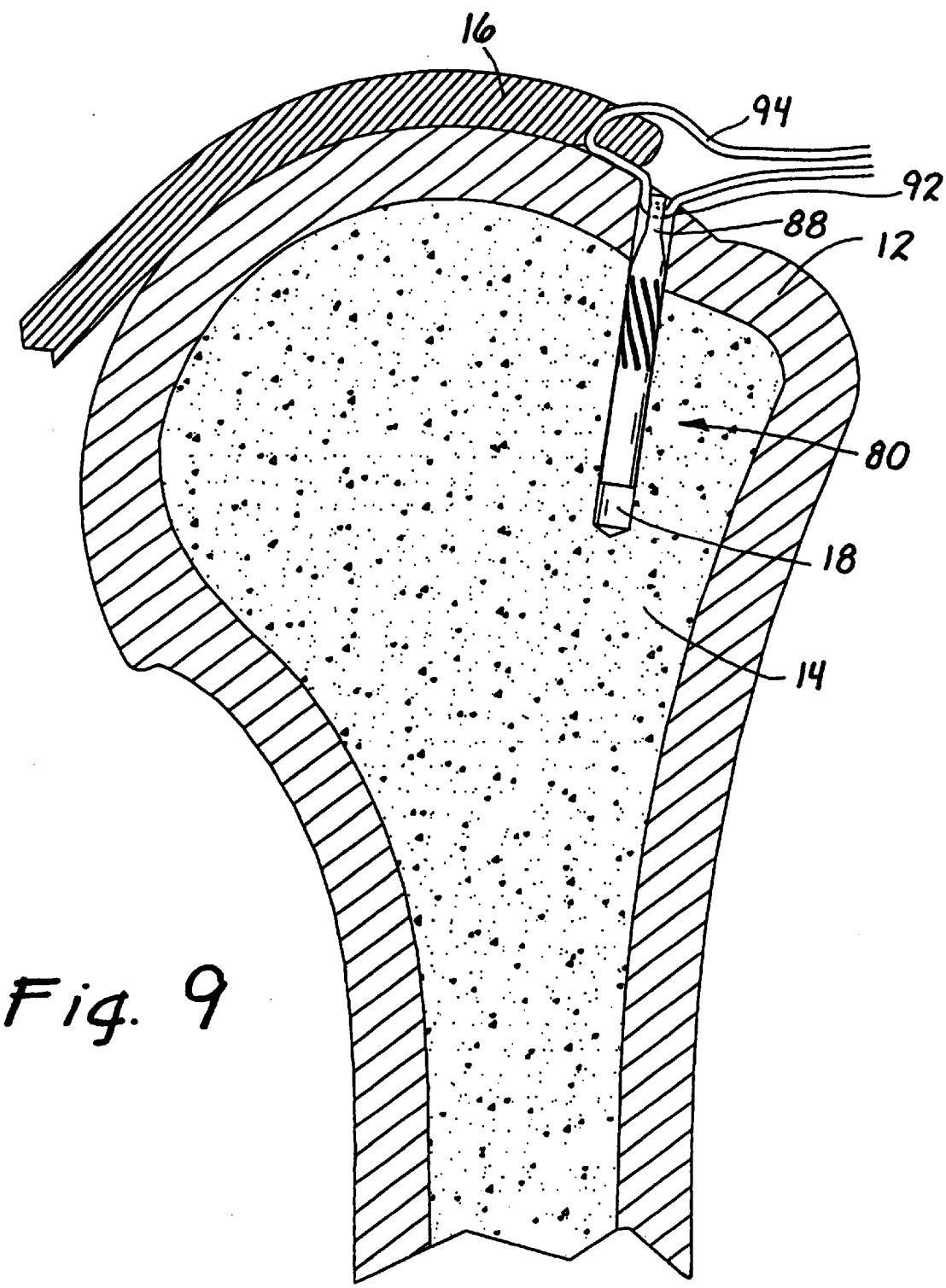
FIG. 9 is a cross-sectional plan view of a humerus and tendon showing the anchor of FIG. 7 inserted into the humerus of FIG. 1, in accordance with a method of the present invention.
Figure 10:
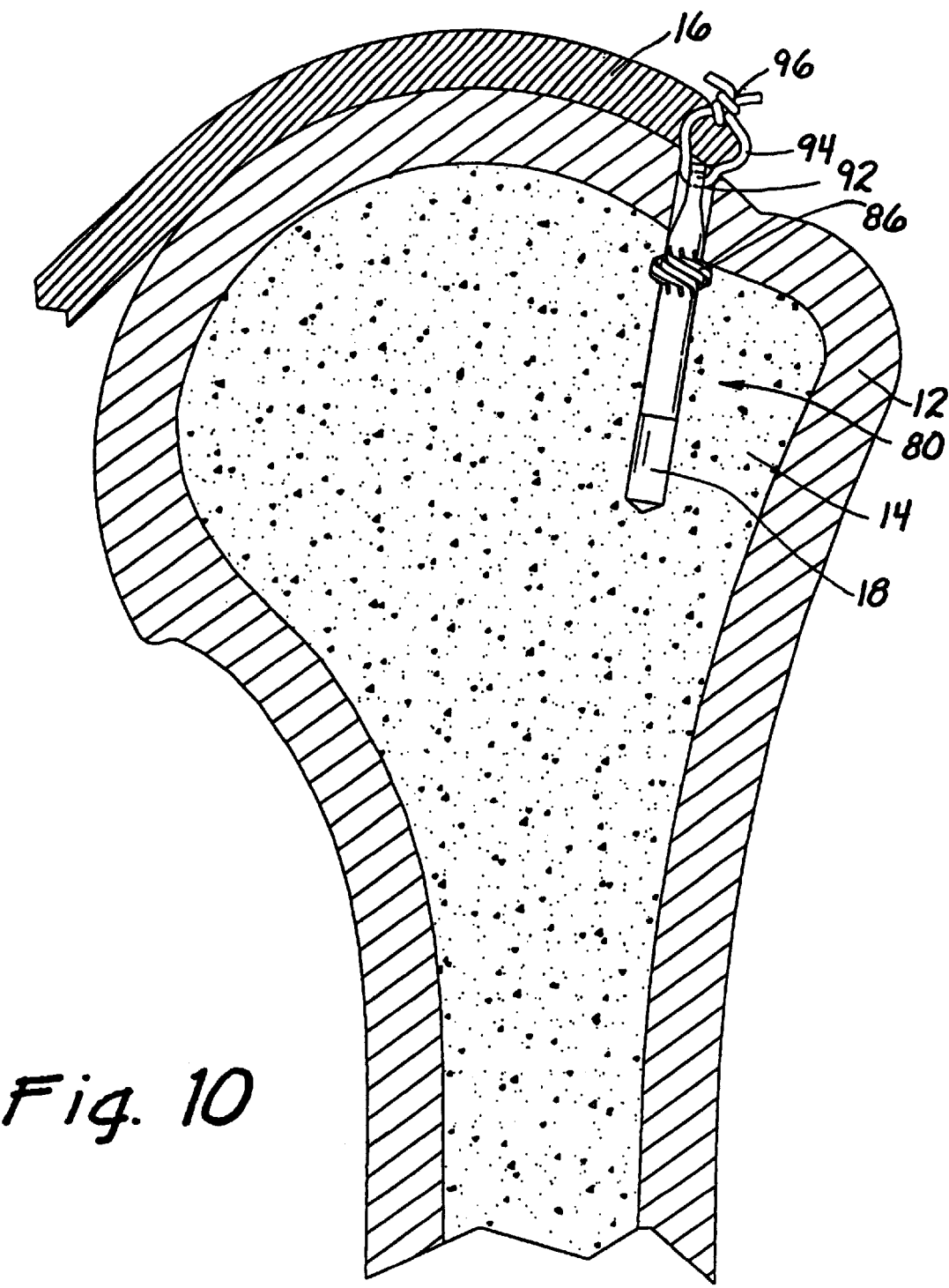
FIG. 10 is a cross-sectional plan view similar to FIG. 9, showing the anchor in a deployed state and the tendon sutured to the humeral bone.

Referring now to FIGS. 9–10, there may be seen a cross section of a humeral head 10 identical to that described in connection with previous FIGS. 1, 5 and 6. The bone anchor 80 has been disposed within the drilled hole 18, with the proximal end entirely below the surface of the cortical bone 12. A length of suture 94 is shown threaded through the suture conduit 92 at the proximal end 88 of the bone anchor 80. The length of suture 94 is also shown threaded through the rotator cuff tendon 16 laying on top of the humeral head 10. As shown particularly in FIG. 10, the bone anchor 80 has been deployed by the application of a compressive force to create the characteristic bending of the ribs 86 into their semi-circular state. The creation of this semi-circular geometry in the ribs 86 increases the body diameter of the bone anchor 80 such that the aggregate outside diameter of the deformed ribs 86 is substantially larger than the nominal diameter of the cylindrical body 82. In this manner, the anchor is prevented from passing proximally out of the drilled hole 18 in the hard cortical bone 12, as it is retained up against the inner surface of the cortical bone 12. As discussed supra, the structure is strengthened because of the overlapping expanded ribs 86. A knot 96, tied in the length of suture 94, secures the rotator cuff tendon 16 to the humeral head 10, or, alternatively, another method for tensioning the suture, to thereby approximate the tendon to the bone, may be utilized.

Figure 11:
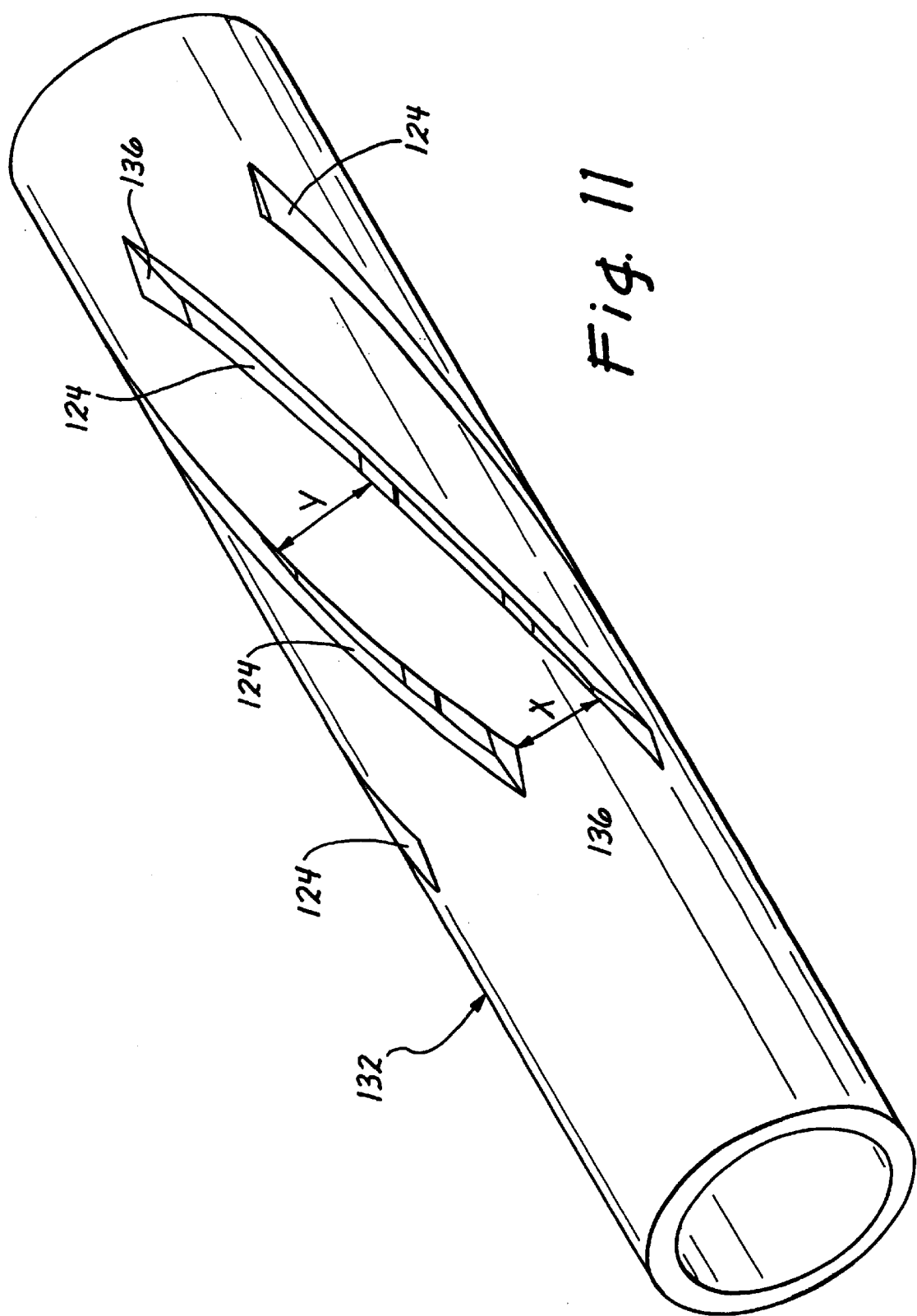
FIG. 11 is a perspective view of an alternative embodiment of the bone anchor shown in FIG. 7.

FIGS. 11 and 12 illustrate yet another alternative embodiment of the bone anchor shown in FIGS. 1–10, which is, at present, a preferred approach for fabricating any of the embodiments shown in FIGS. 1–10. Applicants have discovered, through empirical research, that the cutting techniques used in creating the slits 24, 84 in any of the embodiments of FIGS. 3 and 7, for example, are important in determining the functionality of the resultant anchor. More specifically, Applicants determined that laser-cutting the slits 24, 84, wherein the slits are cut on a helix (meaning that the laser beam is held stationary while the workpiece is rotated), results in a constant spacing between the slits at any point along the length thereof. In such an instance, Applicants have found that it takes a significant compressive force on the cylindrical body 32, 82 to deploy the petals 44, 64.

In FIGS. 11 and 12, there is shown a cylindrical body 132, similar to cylindrical bodies 32, 82 illustrated in FIGS. 1–10, and having a plurality of slits 124 formed therein, similar to slits 24, 84. All aspects of the embodiment shown in FIGS. 11 and 12 are the same as in prior embodiments, except for the specific configuration of the slits 24, and the method by which they are fabricated. In the embodiment of FIGS. 11 and 12, it is preferred that a cutting wheel of a rotating saw is utilized to form the slits 124. Two outcomes of this method of fabrication result in an anchor structure which is deployable upon the application of a substantially lower compressive force, than in the laser-cut embodiments. The first outcome is that each end of each slit 124 is formed with a "notch" or angled surface 136. The second outcome is that, because the cut is straight rather than on a helix, the distance (spacing) between adjacent slits 124 is less at the ends of the slits than in the middle of the slits. As shown in FIG. 11, this means that the distance x between adjacent slits 124 at their respective ends is less than the distance y between the same adjacent slits 124 at their respective middles.

Applicants have determined that one or both of these two separate outcomes result in a configuration which is much easier to deploy than when the slits do not have end notches such as notches 136 and are equally spaced from one another along the entire length of the respective slits.

An alternative to the method described in connection with FIGS. 11 and 12 is to continue to utilize a laser cutting method, but to adjust the fabrication process so that the spacing between the respective ends of adjacent ones of the slits 124 is reduced relative to the spacing between middle portions of the same adjacent slits.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. Apparatus for attaching connective tissue to bone, comprising a body having a longitudinal axis, a proximal end, and a distal end, which is adapted to be inserted into a bone, said body having an outer peripheral wall extending substantially completely about said longitudinal axis and defining an inner lumen, said body including a plurality of spaced slits disposed about said outer peripheral wall, each of said slits having a length and lying at an acute angle relative to said longitudinal axis, wherein a distance x between two adjacent slits at a first location along the length of each of the slits is smaller than a distance y between said two adjacent slits at a second location along the length of each of the slits, and further wherein said plurality of spaced slits is sufficient in number such that when an axial length of said body is shortened, thereby causing a plurality of ribs which are disposed between each of said plurality of slits to each expand radially to form respective petals, each of said petals overlap adjacent ones thereof.

2. The apparatus as recited in claim 1, wherein said acute angle is between 0 and 45 degrees.

3. Apparatus for attaching connective tissue to bone, comprising a body having a longitudinal axis, a proximal end, and a distal end, which is adapted to be inserted into a bone, said body having an outer peripheral wall extending substantially completely about said longitudinal axis and defining an inner lumen, said body including a plurality of spaced slits disposed about said outer peripheral wall, each of said slits having a length and an angled surface at an end thereof, extending depthwise into a wall forming said body, wherein a distance x between two adjacent slits at a first location along the length of each one of the adjacent slits is smaller than a distance y between said two adjacent slits at a second location along the length of each one of said adjacent slits.

4. The apparatus as recited in claim 3, wherein each of said slits has an angled surface at each end thereof, extending depthwise into said wall.

5. The apparatus as recited in claim 3, wherein said first location is proximate to an end of each of the slits and the second location is in a middle region of each of said adjacent slits.

6. A method of fabricating an apparatus for attaching connective tissue to bone, comprising:

making a pattern of a bone anchor using a bio-compatible material;

disposing a plurality of spaced slits across a width of said pattern, adjacent ones of said slits being closer together at first and third location along a length thereof and being father apart at a second location along said length, wherein said location is near a first end and said third location is near a second opposing end of each of said respective adjacent slits, and further wherein said second location is in a middle region of each of said respective adjacent slits; and reforming said pattern into an anchor body.

7. The method as recited in claim 6, wherein said anchor body is a generally cylindrical body.

8. The method as recited in claim 6, and further comprising a step of forming an angled surface extending depthwise into said pattern at an end of each of said spaced slits.

9. The method as recited in claim 8, wherein an angled surface is formed at each end of each of said spaced slits.

10. The method as recited in claim 6, wherein a cutting wheel is used to form said spaced slits.

11. Apparatus for attaching connective tissue to bone, comprising a body having a longitudinal axis, a proximal end, and a distal end, which is adapted to be inserted into a bone, said body including a plurality of spaced slits disposed about said periphery, each of said slits having a length and lying at an acute angle relative to said longitudinal axis, wherein a distance x between two adjacent slits at a first location along the length of each of the slits is smaller than a distance y between said two adjacent slits at a second location along the length of each of the slits, and further wherein said plurality of spaced slits is sufficient in number such that when an axial length of said body is shortened, thereby causing a plurality of ribs which are disposed between each of said plurality of slits to each expand radially to form respective petals, each of said petals overlap adjacent ones thereof.

12. The apparatus as recited in claim 11, wherein said slits each comprise an end, said first location being proximate to an end of each of the adjacent slits and the second location being in a middle region of each of the adjacent slits.

13. The apparatus as recited in claim 11, wherein each of said slits further comprises an angled surface at an end thereof.

14. The apparatus as recited in claim 11, wherein each of said slits further comprises an angled surface at each end thereof, each of said angled surfaces extending depthwise into a wall forming said body.

15. The apparatus as recited in claim 11, wherein said body comprises a cylindrical body, and said peripheral wall comprises an outer circumferential wall.

16. The apparatus as recited in claim 11, wherein said plurality of spaced slits comprises at least six slits.

17. The apparatus as recited in claim 11, wherein when said body is placed in compression, regions of said outer wall between adjacent ones of said spaced slits expand radially to extend into adjacent bone.

* * * * *

UNITED STATES PATENT AND TRADEMARK OFFICE
CERTIFICATE OF CORRECTION

PATENT NO.    : 6,660,008 B1
DATED         : December 9, 2003
INVENTOR(S)   : Foerster et al.

It is certified that error appears in the above-identified patent and that said Letters Patent is hereby corrected as shown below:

Column 8,
Line 16, after "FIG." change "1$a$" to -- 1 a --.

Column 13,
Line 30, change "reforming" to -- forming --.

Signed and Sealed this

Twenty-ninth Day of June, 2004

JON W. DUDAS
*Acting Director of the United States Patent and Trademark Office*